US008346484B2

(12) United States Patent
Ishikawa et al.

(10) Patent No.: US 8,346,484 B2
(45) Date of Patent: *Jan. 1, 2013

(54) SELECTIVE RESONANCE OF CHEMICAL STRUCTURES

(75) Inventors: Muriel Y. Ishikawa, Livermore, CA (US); Edward K. Y. Jung, Bellevue, WA (US); Nathan P. Myhrvold, Medina, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 985 days.

This patent is subject to a terminal disclaimer.

(21) Appl. No.: 12/313,411

(22) Filed: Nov. 19, 2008

(65) Prior Publication Data

US 2009/0081800 A1   Mar. 26, 2009

Related U.S. Application Data

(60) Continuation-in-part of application No. 11/260,467, filed on Oct. 26, 2005, and a division of application No. 11/186,632, filed on Jul. 21, 2005, and a continuation-in-part of application No. 11/186,635, filed on Jul. 21, 2005, now Pat. No. 8,112,233, and a continuation-in-part of application No. 11/186,394, filed on Jul. 21, 2005, and a continuation-in-part of application No. 11/186,633, filed on Jul. 21, 2005, now Pat. No. 7,979,213, and a continuation-in-part of application No. 11/186,634, filed on Jul. 21, 2005, and a continuation-in-part of application No. 11/186,631, filed on Jul. 21, 2005, and a continuation-in-part of application No. 11/186,912, filed on Jul. 21, 2005, now abandoned.

(51) Int. Cl.
*G01N 33/48* (2006.01)

(52) U.S. Cl. .......................................... 702/19

(58) Field of Classification Search ...................... 702/19
See application file for complete search history.

(56) References Cited

U.S. PATENT DOCUMENTS

| | | | |
|---|---|---|---|
| 4,973,848 A | 11/1990 | Kolobanov et al. |
| 5,304,113 A | 4/1994 | Sieber et al. |
| 5,317,156 A | 5/1994 | Cooper et al. |
| 5,702,432 A | 12/1997 | Chen et al. |
| 5,850,629 A | 12/1998 | Holm et al. |
| 6,022,479 A | 2/2000 | Smirnov |
| 6,190,691 B1 | 2/2001 | Mak |
| 6,214,033 B1 | 4/2001 | Ii et al. |
| 6,454,789 B1 | 9/2002 | Chen et al. |
| 6,484,052 B1 | 11/2002 | Visuri et al. |
| 6,485,437 B1 | 11/2002 | Tapper |
| 6,527,716 B1 | 3/2003 | Eppstein |
| 6,602,274 B1 | 8/2003 | Chen |
| 6,607,525 B2 | 8/2003 | Franco |
| 6,643,544 B1 | 11/2003 | Adachi et al. |
| 6,645,230 B2 | 11/2003 | Whitehurst |
| 6,664,228 B1 | 12/2003 | Moser et al. |
| 6,733,451 B2 | 5/2004 | Rabiner et al. |
| 6,898,533 B1 | 5/2005 | Miller et al. |
| 6,899,723 B2 | 5/2005 | Chen |
| 6,986,782 B2 | 1/2006 | Chen et al. |
| 7,009,362 B2 | 3/2006 | Tsukamoto et al. |
| 7,018,395 B2 | 3/2006 | Chen |
| 2002/0010414 A1 | 1/2002 | Coston et al. |
| 2002/0183682 A1 | 12/2002 | Darvish et al. |
| 2003/0097090 A1 | 5/2003 | Mori et al. |
| 2003/0208235 A1 | 11/2003 | Miller et al. |
| 2003/0229456 A1 | 12/2003 | Beger et al. |
| 2005/0021243 A1 | 1/2005 | Dantus et al. |
| 2006/0010117 A1 | 1/2006 | Bonabeau et al. |
| 2006/0063188 A1 | 3/2006 | Zanni et al. |
| 2006/0173275 A1 | 8/2006 | Van Nesselrooij et al. |
| 2006/0184516 A1 | 8/2006 | Ellis |
| 2007/0021458 A1 | 1/2007 | Ishikawa et al. |

FOREIGN PATENT DOCUMENTS

| | | |
|---|---|---|
| CA | 2482934 A1 | 10/2003 |
| CA | 2584970 A1 | 2/2006 |
| WO | WO 2005/001775 A1 | 1/2005 |

OTHER PUBLICATIONS

Hochstrasser, "Electric Field Effects on Oriented Molecules and Molecular Crystals," Electric Field Effects (1973) vol. 6, pp. 263-269.*
Albini, Angelo; Monti, Sandra; "Photophysics and photochemistry of fluoroquinolones"; Chemical Society Reviews; Bearing dates of May 9, 2003, and Dec. 23, 2002; pp. 238-250; vol. 32; The Royal Society of Chemistry.
Andrews, D.L.; Crisp, R.G., "Laser-Induced Vibrational Frequency Shift", pp. 1-4, located at http://xxx.lanl.gov/ftp/physics/papers/0502/0502136.pdf, bearing a date of Feb. 25, 2005, printed on Mar. 3, 2005.
Callaway, Edward M; Yuste, Rafael; "Stimulating neurons with light"; Current Opinion in Neurobiology; published online Sep. 20, 2002; pp. 587-592; vol. 12; Elsevier Science Ltd.
Chergui, Majed; "Controlling Biological Functions"; Science; bearing a date of Sep. 1, 2006; pp. 1246-1247; vol. 313; AAAS.

(Continued)

*Primary Examiner* — Jerry Lin

(57) ABSTRACT

Chemical compositions may be selectively or preferentially excited by the application of scores comprising a series of energy inputs. A method of characterizing such compositions includes identifying a group of resonant structures where one structure has a resonant frequency that is shiftable by exciting another resonant frequency, determining the necessary frequencies to shift the resonant structure, and applying the set of frequencies to the environment of the target composition.

37 Claims, 10 Drawing Sheets

OTHER PUBLICATIONS

Dian, Brian C.; Longarte, Asier; Zwier, Timothy S.; "Conformational Dynamics in a Dipeptide After Single-Mode Vibrational Excitation"; Science; bearing a date of Jun. 28, 2002; pp. 2369-2373; vol. 296.

Field, R.W.; Revelli, M.A.; Capelle, G.A.. "Optical-optical double resonance laser spectroscopy of BaO", Journal of Chemical Physics, pp. 1-2, located at http://adsabs.harvard.edu/cgi-bin/nph-bib_query?1975JChPh..63.3228F, bearing a date of Oct. 15, 1975, printed on Dec. 13, 2004.

Hasan, Tayyaba; Khan, Ahsan U.; "Phototoxicity of the tetracyclines: Photosensitized emission of singlet delta dioxygen"; Proceedings of the National Academy of Sciences; Bearing dates of Jul. 1986, Jan. 23, 1986 and 1986; pp. 4604-4606; vol. 83.

International Search Report for International Application No. PCT/US06/30815, bearing a mailing date of May 23, 2007.

JLAB.ORG; "2006 News Release, Free-Electron Laser Targets Fat"; Bearing dates of Apr. 10, 2006 and Apr. 21, 2006; pp. 1-6; located at http://www.jlab.org/news/releases/2006/fel.html; printed on May 26, 2006.

Korotkov, Alexander N., "Simple quantum feedback of a solid-state qubit", pp. 1-5, located at http://lanl.arxiv.org/PS_cache/cond-mat/pdf/0404/0404696.pdf, bearing a date of Apr. 30, 2004, printed on Mar. 3, 2005.

Lacher, J.R.; Bitner, J.L.; Park, J.D.; "The Infrared Absorption Spectra of Some Antibiotics in Antimony Trichloride Solution"; Bearing a date of Jan. 19, 1955; pp. 610-614; vol. 59.

Michigan State University, "Infrared Spectroscopy", pp. 1-8, located at http://www.cem.msu.edu/%7Ereusch/VirtualText/Spectrpy/InfraRed/infrared.htm, printed on Dec. 13, 2004.

Prokhorenko, Valentyn I.; Nagy, Andrea M.; Waschuk, Stephen A.; Brown, Leonid S.; Birge, Robert R.; Miller, R. J. Dwayne; "Coherent Control of Retinal Isomerization in Bacteriorhodopsin"; Science; bearing a date of Sep. 1, 2006; pp. 1257-1261; vol. 313.

Rosario-Jansen, Theresa; Jiang, Ru-Tai; Tsai, Ming-Daw; Hanahan, Donald J.; "Phospholipids Chiral at Phosphorus. Synthesis and Stereospecificity of Phosphorothioate Analogues of Platelet-Activating Factor"; Biochemistry; bearing a date of 1988; pp. 4619-4624; vol. 27, No. 13; American Chemical Society.

Schneider, S; Brehm, G; Schmitt, M; Leypold, C; Matousek, P; Towrie, M; "Picosecond time-resolved fluorescence of Tetracycline and its complexes with $Mg^{++}$ or $Ca^{++}$"; Lasers for Science Facility Programme-Chemistry, Central Laser Facility Annual Report; Bearing dates of 2002 and 2001; pp. 103-105.

Schrader, Tobias E.; Schreier, Wolfgang J.; Cordes, Thorben; Koller, Florian O.; Babitzki, Galina; Denschlag, Robert; Renner, Christian; Loweneck, Markus; Dong, Shou-Liang; Moroder, Luis; Tavan, Paul; Zinth, Wolfgang; "Light triggered β-hairpin folding and unfolding"; Proceedings of the National Academy of Sciences of the United States of America; bearing a date of Oct. 2, 2007; pp. 15729-15734; vol. 104, No. 40; The National Academy of Sciences of the USA.

Sheffield Hallam University School of Science and Mathematics, "Infra-Red Absorption Spectroscopy", pp. 1-3, located at http://www.shu.ac.uk/schools/sci/chem/tutorials/molspec/irspec1.htm, printed on Dec. 13, 2004.

Oleinick et al.; "The Role of Apoptosis in Response to Photodynamic Therapy: What, Where, Why and How"; The Royal Society of Chemistry and Owner Societies; bearing a date of 2002; pp. 1-21; vol. 1; Photochem. Photobiol. Sci. (2002).

Sessler et al.; "Texaphyrins New Drugs with Diverse Clinical Applications in Radiation and Photodynamic Therapy"; Biochemical Pharmacology; bearing a date of 2000; pp. 733-739; vol. 59; Elsevier Science Inc.

Sharman et al.; "Targeted Photodynamic Therapy via Receptor Mediated Delivery Systems"; Advanced Drug Delivery Reviews; bearing a date of 2003; pp. 53-76; vol. 56 (2004); Elsevier B.V.

Straubinger, Reinhard K.; "PCR-Based Quantification of *Borrelia burgdorferi* Organisms in Canine Tissues over a 500-Day Postinfection Period"; Journal of Clinical Microbiology; vol. 38, No. 6; bearing a date of Jun. 2000; pp. 2191-2199; American Society for Microbiology.

Barton, Jennifer Kehlet et al.; "Cooperative Phenomena in Two-pulse, Two-color Laser Photocoagulation of Cutaneous Blood Vessels"; Photochemistry and Photobiology; bearing a date of 2001; pp. 642-650; vol. 73, Issue 6; American Society for Photobiology.

Crispien, Kai et al.; "Using Spatial Audio for the Enhanced Presentation of Synthesised Speech within Screen-Readers for Blind Computer Users"; Lecture Notes in Computer Science; bearing a date of 1994; pp. 144-153; vol. 860.

Levis, Robert J. et al.; "Selective Bond Dissociation and Rearrangement with Optimally Tailored, Strong-Field Laser Pulses"; Science; bearing a date of Apr. 27, 2001; pp. 709-713; vol. 292; located at www.sciencemag.org.

MacBeath, Gavin et al.; "Printing Proteins as Microarrays for High-Throughput Function Determination"; Science; Sep. 8, 2000; pp. 1760-1763; vol. 289; located at www.sciencemag.org.

Shlien, Seymour; "The Modulated Lapped Transform, Its Time-Varying Forms, and Its Applications to Audio Coding Standards"; IEEE Transactions on Speech and Audio Processing; Jul. 1997; pp. 359-366; vol. 5, No. 4; IEEE.

Babincová, M. et al.; "AC-magnetic field controlled drug release from magnetoliposomes: design of a method for site-specific chemotherapy"; Bioelectrochemistry; bearing a date of 2002; pp. 17-19; vol. 55; Elsevier Science B.V.

Moroz, P. et al; "Tumor Response to Arterial Embolization Hyperthermia and Direct Injection Hyperthermia in a Rabbit Liver Tumor Model"; Journal of Surgical Oncology; bearing a date of 2002; pp. 149-156; vol. 80; Wiley-Liss, Inc.

Holick, Michael F.; "The Cutaneous Photosynthesis of Previtamin $D_3$: A Unique Photoendocrine System"; The Journal of Investigative Dermatology; bearing a date of Jul. 1981; pp. 51-58; vol. 77, No. 1; © 1981 The Williams & Wilkins Co.

Ichihashi, M. et al.; "UV-induced skin damage"; Toxicology; bearing a date of 2003; pp. 21-39; vol. 189; © 2003 Elsevier Science Ireland Ltd.

Ogawa, S. et al.; "Brain Magnetic resonance imaging with contrast dependent on blood oxygenation"; Proc. Natl. Acad. Sci. USA Biophysics; bearing a date of Dec. 1990; pp. 9868-9872; vol. 87.

Evseev, A. V. et al.; "Highly Selective and Efficient Multiphoton Dissociation of Polyatomic Molecules in Multiple-Frequency IR-Laser Fields"; Appl. Phys. B: Photo-physics and Laser Chemistry; bearing a date of 1985; pp. 93-103; Springer-Verlag.

Hansen, Ernil; "Cell Salvage in the Presence of Malignancy"; Transfusion Alternatives in Transfusion Medicine; bearing a date of Dec. 2003; pp. 472-477; vol. 5, No. 5.

Kereiakes, Dean J. et al.; "Phase I Drug and Light Dose-Escalation Trial of Motexafin Lutetium and Far Red Light Activation (Phototherapy) in Subjects With Coronary Artery Disease Undergoing Percutaneous Coronary Intervention and Stent Deployment: Procedural and Long-term Results"; Circulation: Journal of the American Heart Association; bearing a date of 2003; pp. 1310-1315; 108; American Heart Association.

Park, Youmie et al.; "Application of Fourier Transform Ion Cyclotron Resonance Mass Spectrometry to Oligosaccharides"; Mass Spectrometry Reviews; bearing a date of 2005; pp. 232-264; 24; Wiley Periodicals, Inc.

Vargas, Franklin et al.; "The photochemistry of dipyridamole"; Journal of Photochemistry and Photobiology A: Chemistry; bearing a date of 2002; pp. 237-243; 153; Elsevier Science B.V.

Yoon, Sangwoon et al.; "Vibrationally Controlled Chemistry: Mode- and Bond-Selected Reaction of $CH_3D$ with $Cl^+$"; J. Phys. Chem. B; bearing a date of 2005; pp. 8388-8392; 109; American Chemical Society.

Harrison et al.; "Estimation of body composition: a new approach based on electromagnetic principles"; The American Journal of Clinical Nutrition; bearing a date of May 1982; pp. 1176-1179; vol. 35; © 1982 American Society for Clinical Nutrition; downloaded from www.ajcn.org; printed Aug. 2, 2009.

Antes, J. et al.; "Analysis and Improvement of Strong Exothermic Nitrations in Microreactors"; Trans IChemE, Aug. 2003; pp. 760-765; vol. 81, Part A; Institution of Chemical Engineers.

Dougherty, Thomas J. et al.; "Review: Photodynamic Therapy"; Journal of the National Cancer Institute; Jun. 17, 1998; pp. 889-905; vol. 90, No. 12; Oxford University Press.

Roy, Indrajit et al.; "Ceramic-Based Nanoparticles Entrapping Water-Insoluble Photosensitizing Anticancer Drugs: A Novel Drug- Carrier System for Photodynamic Therapy"; J. Am. Chem. Soc.; bearing a date of Jun. 10, 2003; pp. 7860-7865; vol. 125, No. 26; American Chemical Society.

Fuß et al.; "IR Multiphoton Absorption and Isotopically Selective Dissociation of $CHClF_2$ in a Herriott Multipass Cell"; Zeitschrift Fur Physik D.; bearing a date of 1994, final version submitted Oct. 21, 1993; pp. 291-298; vol. 29; Springer-Verlag.

Anzali, Soheila et al.; "Discriminating between Drugs and Nondrugs by Prediction of Activity Spectra for Substances (PASS)"; Journal of Medicinal Chemistry; bearing at date of Jun. 14, 2001; pp. 2432-2437; vol. 44, No. 15; American Chemical Society.

Canadian Intellectual Property Office; Canadian Office Action; App. No. 2,653,245; Aug. 20, 2012 (received by our agent on Aug. 24, 2012); pp. 1-5.

Drobizhev et al.; "Understanding Strong Two-Photon Absorption in π-Conjugated Porphyrin Dimers Via Double-Resonance Enhancement in a Three-Level Model"; J. Am. Chem. Soc.; bearing a date of 2004, received Sep. 7, 2004; pp. 15352-15353; vol. 126, No. 47; American Chemical Society.

Fournier et al.; "Ultrafast Studies of the Excited-State Dynamics of Copper and Nickel Phthalocyanine Tetrasulfonates: Potential Sensitizers for the Two-Photon Photodynamic Therapy of Tumors"; Photochem. Photobiol. Sci.; bearing a date of 2004, received Mar. 10, 2003; pp. 120-126; vol. 3; The Royal Society of Chemistry and Owner Societies 2004.

* cited by examiner

SELECTIVE RESONANCE OF CHEMICAL STRUCTURES

CROSS-REFERENCE TO RELATED APPLICATIONS

The present application is related to, claims the earliest available effective filing date(s) from (i.e., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The United States Patent Office (USPTO) has published a notice to the effect that the USPTO's computer programs require that patent applicants reference both a serial number and indicate whether an application is a continuation or continuation-in-part. The present applicant entity has provided below a specific reference to the application(s) from which priority is being claimed as recited by statute. Applicant entity understands that the statute is unambiguous in its specific reference language and does not require either a serial number or any characterization such as "continuation" or "continuation-in-part." Notwithstanding the foregoing, applicant entity understands that the USPTO's computer programs have certain data entry requirements, and hence applicant entity is designating the present application as a continuation-in-part of its parent applications, but expressly points out that such designations are not to be construed in any way as any type of commentary and/or admission as to whether or not the present application contains any new matter in addition to the matter of its parent application(s).

RELATED APPLICATIONS

For purposes of the USPTO extra-statutory requirements, the present application constitutes a continuation-in-part of currently co-pending U.S. patent application Ser. No. 11/260,467, entitled SELECTIVE RESONANCE OF CHEMICAL STRUCTURES, naming Muriel Y. Ishikawa, Edward K. Y. Jung, Nathan P. Myhrvold, and Lowell L. Wood, Jr. as inventors, filed 26 Oct. 2005, which is currently co-pending, or is an application of which a currently co-pending application is entitled to the benefit of the filing date.

For purposes of the USPTO extra-statutory requirements, the present application constitutes a divisional of currently co-pending U.S. patent application Ser. No. 11/186,632, entitled SELECTIVE RESONANCE OF CHEMICAL STRUCTURES, naming Muriel Y. Ishikawa, Edward K. Y. Jung, Nathan P. Myhrvold, and Lowell L. Wood, Jr. as inventors, filed 21 Jul. 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/186,635, entitled SELECTIVE RESONANCE OF CHEMICAL STRUCTURES, naming Muriel Y. Ishikawa, Edward K. Y. Jung, Nathan P. Myhrvold, and Lowell L. Wood, Jr. as inventors, filed 21 Jul. 2005 now U.S. Pat. No. 8,112,233, or is an application of which a currently co-pending application is entitled to the benefit of the filing date.

For purposes of the USPTO extra-statutory requirements, the present application constitutes a continuation-in-part of currently co-pending U.S. patent application Ser. No. 11/186,394, entitled SELECTIVE RESONANCE OF CHEMICAL STRUCTURES, naming Muriel Y. Ishikawa, Edward K. Y. Jung, Nathan P. Myhrvold, and Lowell L. Wood, Jr. as inventors, filed 21 Jul. 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/186,633, entitled SELECTIVE RESONANCE OF CHEMICAL STRUCTURES, naming Muriel Y. Ishikawa, Edward K. Y. Jung, Nathan P. Myhrvold, and Lowell L. Wood, Jr. as inventors, filed 21 Jul. 2005 now U.S. Pat. No. 7,979,213, or is an application of which a currently co-pending application is entitled to the benefit of the filing date.

For purposes of the USPTO extra-statutory requirements, the present application constitutes a continuation-in-part of currently co-pending U.S. patent application Ser. No. 11/186,634, entitled SELECTIVE RESONANCE OF CHEMICAL STRUCTURES, naming Muriel Y. Ishikawa, Edward K. Y. Jung, Nathan P. Myhrvold, and Lowell L. Wood, Jr. as inventors, filed 21 Jul. 2005, which is currently co-pending, or is an application of which a currently co-pending application is entitled to the benefit of the filing date.

For purposes of the USPTO extra-statutory requirements, the present application constitutes a continuation-in-part of currently co-pending U.S. patent application Ser. No. 11/186,631, entitled SELECTIVE RESONANCE OF CHEMICAL STRUCTURES, naming Muriel Y. Ishikawa, Edward K. Y. Jung, Nathan P. Myhrvold, and Lowell L. Wood, Jr. as inventors, filed 21 Jul. 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/186,912, entitled SELECTIVE RESONANCE OF CHEMICAL STRUCTURES, naming Muriel Y. Ishikawa, Edward K. Y. Jung, Nathan P. Myhrvold, and Lowell L. Wood, Jr. as inventors, filed 21 Jul. 2005 now abandoned, or is an application of which a currently co-pending application is entitled to the benefit of the filing date.

SUMMARY

In one aspect, a method of applying energy to a selected group of proximate atoms within a medium comprises selecting a score specifying a series of differing energy inputs, and applying the series of differing energy inputs specified by the score to the medium. As will be described further herein, the term "differing" is not necessarily restricted to energy inputs from different source mechanisms, energy inputs at different frequencies, or temporally or spatially non-overlapping energy inputs.

The differing energy inputs of the series are selected to resonate each resonant structure of a plurality of resonant structures among the group of proximate atoms. The score may be selected so that applying the series of differing energy inputs has a physical effect, such as transferring substantially more energy to at least a portion of the group of proximate atoms than to other atoms in the medium, breaking a predetermined bond between two members of the group of proximate atoms, or changing a kinetic parameter of a reaction involving a member of the group of proximate atoms. Energy transfer to the medium may be predominantly through resonant excitation of the plurality of resonant structures. The plurality of resonant structures may be resonated simultaneously, sequentially, and/or in a temporally overlapping fashion. The series of differing energy inputs may be applied simultaneously, sequentially, and/or in a temporally overlapping fashion.

The group of proximate atoms may form at least a portion of a molecule (e.g., a biomolecule such as a protein or nucleotide), at least a portion of a crystal, or at least a portion of a complex of molecules. Members of the group of proximate atoms in some cases may be separated by a distance of no more than 300 Å, and/or may be connected directly or indirectly by bonds between the atoms (e.g., covalent, ionic, metallic, van der Waals, hydrogen, coulombic, and/or magnetic attractions). The score may comprise at least 4, at least 10, or at least 36 energy inputs. The plurality of resonant structures may comprise a longitudinal vibrational mode of a bond, a bending mode of two bonds, and/or a squashing mode of a plurality of bonds between members of the group of proximate atoms.

The score may specify application of one or more electromagnetic beams as energy input(s), which may have a characteristic selected from the group consisting of a selected set of frequencies, a selected set of modulation frequencies, a selected set of phases, a selected set of amplitudes, a selected temporal profile, a selected set of polarizations, and a selected direction. The selected set of frequencies and/or the selected set of modulation frequencies may be approximately monochromatic, may comprise a plurality of local maxima, and/or may comprise two frequencies having differing amplitudes. The electromagnetic beam may be coherent or incoherent. The temporal profile may be characterized by a selected beam duration, and/or by a selected change in frequency, modulation frequency, phase, amplitude, polarization, or direction during a selected time interval. The electromagnetic beam may be polarized, amplitude modulated, or frequency modulated, and it may be, for example, an infrared beam. A plurality of electromagnetic beams may differ in frequency, modulation frequency, phase, amplitude, polarization, or direction, and/or may intersect at a target location. The method may include scanning the electromagnetic beam.

The method may also include applying a field to the medium, the field preferentially orienting at least a portion of the group of proximate atoms. The field may be, for example, an electric field, a magnetic field, an electromagnetic field, a mechanical stress, a mechanical strain, a lowered or elevated temperature, a lowered or elevated pressure, a phase change, an adsorbing surface, a catalyst, an energy input, or a combination of any of these.

The plurality of resonant structures may be in an arrangement having two end resonant structures and a center resonant structure, and may be resonated in a sequence beginning from the two end resonant structures and progressing towards the center resonant structure (which may be a temporally overlapping sequence). The group of proximate atoms may undergo a physical effect upon resonance of the center structure. The resonance of the center structure may break a predetermined bond between two members of the group of proximate atoms.

In another aspect, a method of exciting a composition including a plurality of resonant structures, each having a resonant frequency, comprises selecting a set of excitation energies and applying the set of excitation energies to the composition. Each excitation energy has a frequency (e.g., a modulation frequency) matching the resonant frequency of at least one of the resonant structures. Together, the excitation energies cause a chemical change in the composition that would not be caused by the application of any one of the excitation energies applied alone. The excitation energies may be applied simultaneously, sequentially, or in a temporally overlapping fashion. The chemical change in the composition may include, for example, breaking a bond between two atoms of the composition and/or changing a kinetic parameter of a reaction involving the composition. The composition may be a biomolecule (e.g., a protein or nucleotide), a crystal, or a complex of molecules. The set of excitation energies may comprise at least 4, at least 10, or at least 36 excitation energies. The plurality of resonant structures may comprise a longitudinal vibrational mode of a bond, a bending mode of two bonds to an atom, and/or a squashing mode of a plurality of bonds.

The excitation energies may be electromagnetic beams, each of which may have at least one characteristic selected from the group consisting of a selected set of frequencies, a selected set of phases, a selected set of amplitudes, a selected temporal profile, a selected set of polarizations, and a selected direction. The selected set of frequencies may be monochromatic, may comprise a plurality of local maxima, may be Gaussian, or may comprise at least two frequencies having differing amplitudes. At least one of the electromagnetic beams may be coherent or incoherent. The temporal profile may be characterized by a selected beam duration, and/or by a selected change in frequency, modulation frequency, phase, amplitude, polarization, or direction during a selected time interval. At least one electromagnetic beam may be polarized, amplitude modulated, or frequency modulated, and it may be, for example, an infrared beam. A plurality of electromagnetic beams may differ in frequency, modulation frequency, phase, amplitude, polarization, or direction, and/or may intersect at a target location. The method may include scanning at least one electromagnetic beam.

The method may also include applying a field to the medium, the field preferentially orienting at least a portion of the group of proximate atoms. The field may be, for example, an electric field, a magnetic field, an electromagnetic field, a mechanical stress, a mechanical strain, a lowered or elevated temperature, a lowered or elevated pressure, a phase change, an adsorbing surface, a catalyst, an energy input, or a combination of any of these.

The plurality of resonant structures may be in an arrangement having two end resonant structures and a center resonant structure, and may be resonated in a sequence beginning from the two end resonant structures and progressing towards the center resonant structure (which may be a temporally overlapping sequence). The composition may undergo a physical effect upon resonance of the center structure. The resonance of the center structure may break a predetermined bond between two atoms of the composition.

In yet another aspect, a method of selectively exciting resonant structures in a material comprises applying a first excitation energy to the material to excite a first resonant structure, thereby shifting a resonant frequency of a second resonant structure, and applying a second excitation energy to the material to excite the second resonant structure at its shifted resonant frequency. In some cases, the excitation of the second resonant structure at its shifted resonant frequency may shift a resonant frequency of a third resonant structure, and the method may include applying a third excitation energy to the material to excite the third resonant structure at its shifted resonant frequency. The method may also include analogous shifting and exciting of at least 8 additional resonant structures, or of at least 34 additional resonant structures, at their respective shifted resonances. The first and second resonant structures may be at least portions of a molecule (e.g., a biomolecule such as a protein or a nucleotide), a crystal, or a complex of molecules. The first and second resonant structures may be longitudinal vibrational modes of two adjacent bonds, or of two nonadjacent bonds. At least one of the first and second resonant structures may comprise at least two bonds, and/or may be a bending mode or a squashing mode.

At least one of the first and second excitation energies may be an electromagnetic beam (e.g., an infrared beam), which may be amplitude modulated or frequency modulated. The method may include scanning the beam. At least one of the first and second excitation energies may be a plurality of electromagnetic beams, which may differ in polarization or orientation, and which may intersect at a target location.

In still another aspect, a method of characterizing a composition comprises determining a score specifying a series of differing energy inputs, and identifying the composition by the determined score. The differing energy inputs of the specified series are selected to resonate each resonant structure, and application of the differing energy inputs selectively affects the composition. The score may have a physical effect on the composition such as transferring substantially more energy to the composition than to other material to which the set of differing energy inputs is applied, breaking a predetermined bond between two atoms of the composition, and/or changing a kinetic parameter of a reaction involving the composition. The score may be determined, for example, by determining resonant frequencies by computational modeling or by spectroscopy, and/or by applying a plurality of sets of energy inputs to the composition and observing their effects. The method may further include applying the set of energy inputs to the composition. The composition may be a biomolecule, such as a nucleotide or a protein, and the score may specify as many as 4, 10, or 36 energy inputs.

In a further aspect, a method of characterizing a target molecule or group of molecules in an environment comprises identifying a group of resonant structures within the target and determining a score specifying a set of applied frequencies. Each resonant structure in the group possesses at least one characteristic resonant frequency, the characteristic resonant frequency of a shiftable resonant structure in the group can be shifted by exciting a shifting resonant structure in the group, and the group of resonant structures is substantially absent from nontarget molecules in the environment. The applied frequencies of the score, when applied in sequence to the target, shift the characteristic resonant frequency of the shiftable resonant structure through excitation of the shifting resonant structure, excite the shiftable resonant structure at its shifted resonant frequency, and selectively change the energy or state of at least a portion of the target relative to its environment. The method may further comprise applying the set of applied frequencies to the environment of the target molecule. The set of applied frequencies, when applied in sequence to the target, shift the resonance of and excite a plurality of the resonant structures at their respective shifted resonances. Determining a set of applied frequencies may include computational modeling of the target, spectroscopically observing the target, and/or applying a plurality of sets of applied frequencies to the environment and observing their effects on the target. The target may comprise a biomolecule (e.g., a nucleotide or a protein). The identified group of resonant structures may include as many as 4, 10, or 36 resonant structures, and/or may be contiguous within a molecule. The shiftable resonant structure and the shifting resonant structure may or may not share an atom.

In a still further aspect, an instrument for determining a score specifying a series of energy inputs having a physical effect on a target composition includes a test score generator, an energy input component, and a monitor. The test score generator selects a test score for application to the target composition. The energy input component applies the energy inputs specified by the test score to the target composition. The monitor tests whether the target composition has been physically affected by the application of the energy inputs specified by the test score. The test score may comprise a set of energy input descriptors, each descriptor specifying frequency, modulation frequency, phase, amplitude, temporal profile, polarization, direction, and/or coherence. The test score generator may select a test score using a spectroscopic profile of the specimen, molecular modeling, a database of scores, and/or feedback from the monitor. The monitor may measure a property of the target composition such as energy levels, kinetic effects, structural changes, chemical activities, index of refraction, diffraction properties, optical absorption, and/or temperature, and may include a thermal imager and/or a sensor that monitors an optical beam directed at the target composition.

In yet a further aspect, a blood therapy device comprises an energy input component adapted to be placed on or in a human or animal body. The energy input component directs a set of differing energy inputs towards a blood vessel, wherein they selectively resonate a plurality of resonant structures in a target composition in the blood. The blood therapy device may also include a monitor that observes effects of the resonance of the plurality of resonant structures. The resonance may modify or destroy the target composition (e.g., a virus, a biomolecule such as a protein, sugar, triglyceride, or cholesterol, and/or a pharmaceutical such as heparin). The energy input component may direct the set of differing energy inputs through the skin, and/or via an implanted energy transmission device such as an optical fiber.

In an additional aspect, an instrument for determining a score specifying a series of energy inputs having a physical effect on a target composition comprises a modeling tool and a score generator. The modeling tool computationally determines resonant properties of the target composition based on its molecular structure and identifies a series of energy inputs expected to selectively resonate resonant structures of the target composition. The score generator creates a descriptor of the identified series of energy inputs, specifying frequency, modulation frequency, phase, amplitude, temporal profile, polarization, direction, and/or coherence. The descriptor is readable by an instrument for applying the identified series of energy inputs to a composition.

In a further aspect, a chemical agent for therapeutic use comprises a composition having a characteristic set of proximate bonds selectively responsive to a predetermined series of energy inputs. The response of the composition to the predetermined series of energy inputs is selected from the group consisting of breaking one or more bonds of the composition, ablating material surrounding the composition, heating material surrounding the composition, and reacting with material surrounding the composition. The chemical agent may have an affinity for a selected substance or tissue in vivo, or be bound to a carrier having a similar affinity. The predetermined series of energy inputs may include an energy input at a frequency to which living tissue is substantially transparent, which may be, for example, frequency modulated or amplitude modulated. The energy inputs may be applied simultaneously, sequentially, and/or in a temporally overlapping fashion, and the series may comprise as many as 4, 10, or 36 energy inputs.

A method of introducing an agent to a selected tissue may include placing the chemical agent in an animal or human body comprising the selected tissue and applying the score to the body. For example, the chemical agent may be introduced by injection into the tissue, by introduction into the body (e.g., orally, by injection into the bloodstream or the lymphatic system, or by inhalation) and accumulation at the tissue, and/or by placing a carrier bound to the chemical agent in the body. Application of the score may cause the chemical agent to ablate the surrounding tissue.

In yet another aspect, a library of excitation energy specifications includes a structured data repository comprising a plurality of score records. Each score record comprises descriptors for a plurality of energy inputs and a descriptor for an associated composition affected by the plurality of energy inputs, each energy input descriptor specifying frequency, modulation frequency, phase, amplitude, temporal profile, polarization, and/or direction. The library may also include a search engine that allows a user to search for a score record, for example by composition, chemical structure, or energy input descriptor. The library may also include an input component that allows a user to add a score record to the structured data repository, or an output component that allows a user to download a score record. The energy input descriptors and/or the score records may be stored in a tagged data file format such as XML. The score records may also comprise a descriptor describing the effect of the plurality of energy inputs on the composition.

A method of screening for a composition in a medium may comprise accessing the library to locate a score for the composition, applying the energy inputs described by the energy descriptors of the located score to the medium, and observing the medium for reaction of the composition to the applied energy inputs. A method of exciting a composition in a medium may comprise accessing the library to locate a score for the composition and applying the energy inputs of the located score to the medium, wherein the effect of the plurality of energy inputs is to excite the composition. This excitation may destroy the composition.

In yet another aspect, a method of resonating a selected composition in a medium includes accessing a database of score records, selecting a score record from the database, and applying a series of differing energy inputs from the score record to the medium. Each score record of the database specifies a series of differing energy inputs and a composition comprising a plurality of resonant structures, the differing energy inputs of the series being selected to resonate each resonant structure of the plurality of resonant structures of the composition. A score record may specify a plurality of compositions. The selected score record may specify the selected composition, or may specify a composition having a common functional group with the selected composition.

In yet still a further aspect, an instrument for exciting chemical compositions may include an interpreter, and an energy input component (e.g., a laser). The interpreter converts a score comprising a plurality of energy input descriptors into control instructions for the energy input component, which directs energy input into a medium in accordance with the generated control instructions. Each energy descriptor may include a description of frequency, modulation frequency, phase, amplitude, temporal profile, polarization, direction, and/or coherence. The energy input component may include a beam control element (e.g., a reflector, a polarizer, an optical fiber, and/or a lens) that directs or modifies the beam. The instrument may also include a score location component that selects a score to be converted by the interpreter. The score location component may select the score from a library of scores, each score of the library being associated with one or more compositions upon which the score has a physical effect. Scores from the library may include a descriptor of the physical effect, and the library may be remote from the energy input component. The interpreter may include a controller that receives the score from a source. The instrument may also include a monitor in communication with the controller, and the controller may adjust the score converted by the interpreter in response to an observation by the monitor.

The instrument may also include an input component that allows a user to specify a score to be converted by the interpreter, and/or an input component that allows a user to specify a composition or structure and a lookup component that determines a score that describes a set of energy inputs having a physical effect on the specified composition or structure and passes the determined score to the interpreter for conversion. The lookup component may access a library of scores associated with composition(s), which may be remote from the energy input component. The lookup component may present the score to the user for approval (e.g., visually or audibly) before passing it to the interpreter. Audible presentation may include mapping energy input frequencies to audible frequencies for playback to the user.

In still a further aspect, a method of communicating score information to a user comprises selecting a first score comprising a first plurality of energy input descriptors, applying a selected mapping of the first plurality of energy input descriptors to a first plurality of user-perceivable signals, and presenting the first plurality of user-perceivable signals to the user. The energy input descriptors comprise an attribute description of frequency, modulation frequency, phase, amplitude, temporal profile, polarization, direction, and/or coherence. The selected mapping may include mapping the attribute description to an audible tone (e.g., mapping energy frequency to tone frequency, energy duration to tone duration, and/or any attribute to timbre). The selected mapping may also or alternatively include mapping the attribute description to a visible signal (e.g., mapping energy frequency to a visible color, energy duration to a display location, and/or any attribute to shape). The method may further include selecting a second score, applying the mapping from the second plurality of energy input descriptors to a second plurality of user-perceivable signals, and presenting the second plurality of user-perceivable signals to a user (e.g., concurrently with the presentation of the first plurality of user-perceivable signals).

DETAILED DESCRIPTION

The term "biomolecule," as used herein, includes without limitation proteins, peptides, amino acids, nucleotides, nucleic acids, carbohydrates, sugars, glycoproteins, lipids, viruses, prions, antibodies, and enzymes, and fragments, derivatives, and modified forms of any of these, and any other naturally-occurring or synthetic molecule or complex of molecules that has a biological activity or that is effective in modulating a biological activity.

The term "bond," as used herein, includes without limitation covalent, ionic, metallic, van der Waals, hydrogen, coulombic, and magnetic attractions, as well as any other attractive force between atoms or other particles.

Figure 1A:
FIGS. 1A, 1B, and 1C illustrate longitudinal, bending, and squashing modes, respectively, of resonant structures.
Figure 1B:
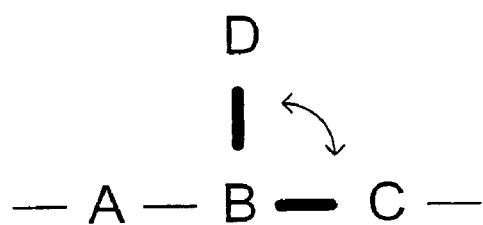
Figure 1C:
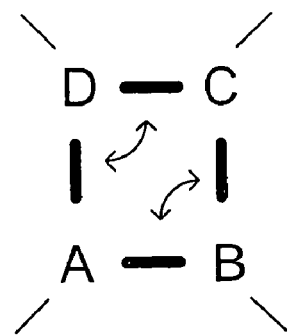

Resonant structures of molecules, crystals, and other compositions have one or more characteristic resonant frequencies, at which they relatively efficiently absorb or otherwise interact with energy applied at matching frequencies. Spectroscopic techniques exploit these characteristic resonances to extract information about chemical structure and properties. For example, covalent bonds typically have a characteristic frequency of longitudinal vibration which depends in significant part upon the masses of the atoms forming the bond and the strength of the bond (e.g., single, double, triple, etc). FIG. 1A shows a single covalent bond between atoms B and C, which may vibrate in such a longitudinal mode. Vibration of ionic bonds is similarly affected by the mass, atomic radius, and charge of the atoms involved. Resonant structures may also be formed by groups of bonds, e.g., in bending or squashing modes (shown in FIGS. 1B and 1C, respectively), each with its own characteristic resonant frequency or frequencies. Crystals may exhibit resonances based on their periodic structures or other properties. Molecule complexes may have resonances that include hydrogen bonds or other attractions between molecules of the complex. The characteristic frequencies of any of these structures may be shifted by a wide variety of factors, including without limitation the properties of adjacent bonds, the excitation state of the molecule or crystal, the presence of defects in a crystal (e.g., free surfaces that cause the resonant properties of "quantum dot" crystallites to depend on their size), stresses in the structure, electric or magnetic fields, or other factors that may influence the properties of the structure. Spectroscopy involves directing energy at a target, and examining the absorbed, transmitted, reflected, and/or emitted frequency spectrum to characterize the physical properties of the target.

Methods are provided herein for directing energy inputs into a target to manipulate or otherwise interact selectively with its structures. In particular, a set of energy inputs analogous to a musical score may be identified, where different "notes" of the score transfer energy with spatio-temporal selectivity to a target composition, for example by resonating different resonant structures. For scores having a sufficient number of notes, high specificity may be obtained, for example wherein compositions having all or most of the corresponding resonant structures are preferentially excited by "playing the score" to the target composition. Even for "short" scores, energy may be efficiently transmitted to a target composition that matches most or all of the resonances identified by the score. Notes as used in this description are not limited to representations of frequency. Notes may also represent, without limitation, amplitudes, polarizations, phase components, gradients, or other characteristics of input energies. While resonance is an exemplary method of transferring energy that can provide spatio-temporal control or other selectivity as discussed below, scores may also include energy inputs that transfer energy to molecules in a nonresonant fashion. For example one or more optical beams, coherent optical pulses, or other controllable inputs can transfer energy selectively to particular portions of a molecule and/or at particular times.

In one aspect, the scores may be used to characterize or identify compositions, as an alternative nomenclature to conventional chemical composition and structure notation. Digital or analog processing, visually presenting, or otherwise processing or treating the scores may indicate or reveal into similarities between compositions that are less readily identified using conventional nomenclature.

Scores having desired effects on particular compositions may be determined by a variety of methods. One starting point for determining a score may be to examine a spectrogram of a composition of interest, since the spectrogram reflects certain resonant responses of the composition. Alternatively, resonances may be calculated by computational methods. Scores may also be determined and/or refined on an empirical basis, using "trial and error" approaches, inferential approaches, observations of trends or other empirical approaches. Typically, such approaches would include applying a candidate score, a portion of a candidate score, or a selected set of notes to a composition and observing the corresponding effects, such as energy absorption, polarization changes, chemical reactions, optical characteristics, vibrations, stresses, changes in electrical or magnetic properties, or other effects. The score, portion of a score, or notes may be applied at an amplitude level that may differ from the level to be used in applying the determined score at a later time. For example, a sample note may be applied at a significantly higher amplitude as part of the characterization than may be appropriate for later applications.

Scores may have a diverse set of potential effects on various compositions. A score may resonate a particular bond in a molecule to breakage, for example, or it may change a kinetic parameter of an affected composition or cause local heating in the vicinity of the composition. In some embodiments, the scores can act as a form of energy catalyst, preferentially shifting the kinetics of selected chemical reactions. For example, a score could alter the kinetics of a chromatography column, causing a reactant to bind or to unbind in response to an applied score. Similarly, a score may alter the migration rate of composition during an electrophoresis process. In this approach, the score may be used to separate stereoisomers during electrophoresis.

Other embodiments include selectively destroying a contaminant or other unwanted composition, such as removing an undesirable metabolic product (e.g., beta-amyloid plaques in Alzheimer's disease patients, gallstones, or kidney stones), a contaminant (e.g., accumulations of tobacco residue in the lungs), a therapeutic agent not desirable for long-term use (e.g., heparin from the blood of dialysis patients downstream of the dialysis unit), or cell type (e.g., cancerous cells) from living tissue, breaking down pollutants in a smokestack, or selectively destroying viruses, either in vivo or in vitro. Still other embodiments include selective repair of biomolecules, e.g., repair of thymine dimers or breaks in the DNA molecule. Unbound base pairs could be specifically excited, or DNA could even be intentionally further damaged in a way selected to trigger the body's own DNA repair mechanism.

An arrangement of inputs that form a score may be analogized to a musical score to aid in understanding some of the aspects. For example, in one approach a score specifies a set of discrete energy inputs, that may be in sequential, parallel, or other arrangements. These inputs may be specified in terms of frequency, modulation frequency, phase, amplitude, temporal profile, polarization, direction, and/or coherence. The set of energy inputs may be played in the form of a "melody" (in which each energy input ends before or as the next begins), in the form of a "chord" (in which all the energy inputs begin and end together), or in a more complex structure, which may include one or more overlapping energy inputs. In addition, the specifications for frequency, modulation frequency, phase, amplitude, polarization, direction, and/or coherence may change over the duration of an energy input. In some embodiments, the energy inputs are electromagnetic beams, such as infrared, visible or ultraviolet beams. The electromagnetic beams may be frequency, phase, amplitude, polarization, pulse width, or otherwise modulated. Such modulation may be applied to the base frequency of the electromagnetic beam or may be applied to a beam envelope. In another approach that may be applied independently or in conjunction with the previously described approaches, two or more beams may provide more flexibility in supplying energy to a selected location, locations, or structures, at frequencies, spatial selectivities, or other parameters, than single source approaches. In one exemplary approach pairs (or larger sets) of inputs can produce beat frequencies, harmonics, interference patterns, or other configurations. In some such configurations and/or combinations, the energy inputs may have frequencies differing from the resonant frequencies of the resonant structures, and yet interact appropriately with the molecules.

While the previously described approaches have been exemplified in terms of additive combinations of energy inputs, in some embodiments, a portion of the series of energy inputs may interact with structures to negate, e.g., by damping or cancellation, rather than enhance, vibrations or other interactions with certain resonant structures. Alternatively or in addition, a structure to which it is desired not to transfer energy may be "deactivated" before, or together with, applying an energy input. For example, the response of the structure may be "deactivated" or otherwise reduced by temporarily bonding it to another structure that changes its resonant frequency or absorbs vibrational energy. In other approaches, locally heating the structure, applying a magnetic or electric field, or applying a local or vector stress or pressure, or otherwise interacting with the structure can change its resonance, or otherwise reduce its response.

When an application of a score involves affecting compositions in a medium (such as but not limited to living tissue), the score may include electromagnetic energy inputs in frequency ranges that penetrate the medium. For example, where a material is contained within a container, the frequencies may be selected where the container is transmissive, yet, the material is responsive. If desired, suitable modulation or beat frequencies may then be used to resonate the resonant structures of the composition.

Figure 2:
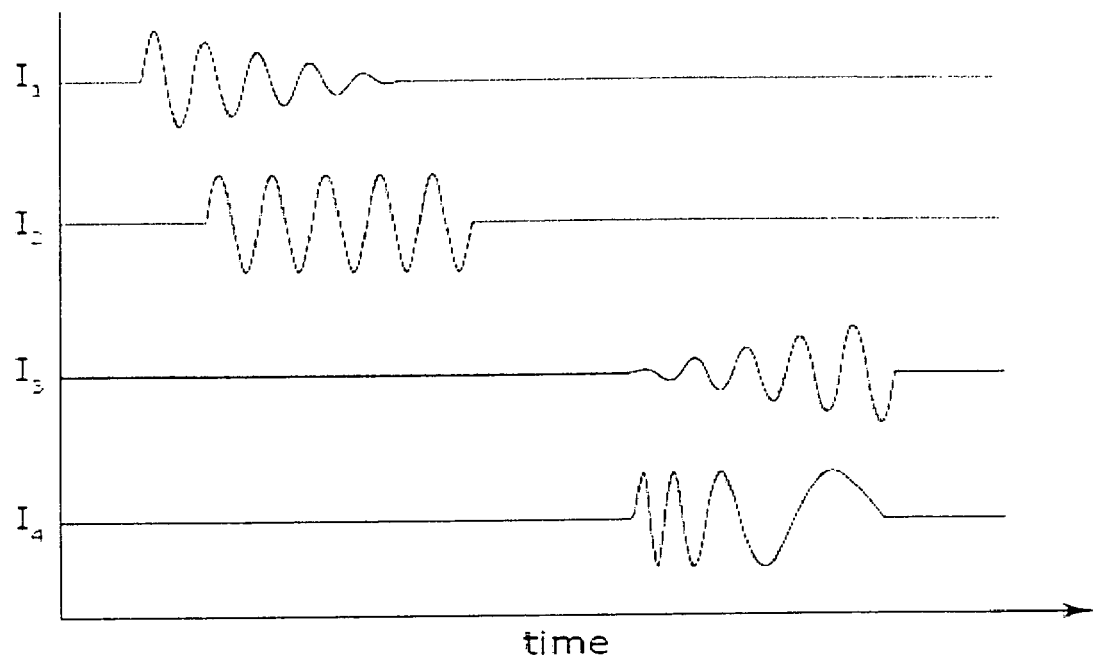
FIG. 2 is a schematic representation of a four-note score.

A schematic of a four-note score illustrating these changes is shown in FIG. 2. Energy inputs $I_1$ and $I_2$ overlap in time, with $I_1$ beginning before $I_2$ begins and ending before $I_2$ ends. $I_1$ has a decreasing amplitude with time, while the amplitude of $I_2$ is substantially constant. $I_3$ and $I_4$ begin at substantially the same time, but $I_3$ terminates before $I_4$. The amplitude of $I_3$ increases with time while maintaining a constant frequency, while the amplitude of $I_4$ stays constant with time while the frequency decreases. Phase, polarization, direction, and coherence are not specified in FIG. 2, but each of these properties may similarly change with time within a single energy input, or differ from one energy input to another. In particular, phase control between multiple beams may provide spatial, temporal, or other specificity that can provide selectivity in resonating only certain structures within a molecule or in targeting molecules having a certain orientation or position. Moreover, polarization of the energy inputs may be useful in distinguishing molecules on the basis of chirality, for example to excite only molecules having a desired chirality. One skilled in the art will recognize that other combinations, including more complex energy inputs may be implemented. For example, frequency and amplitude of an energy input may both be varied. As another example, the frequency and/or amplitude of an energy input may be increased during one time interval and decreased during another. As still another example, an energy input may be "chopped" to provide a sequence of energy input components. Several other approaches to varying amplitude, frequency, duration or other characteristics of the energy inputs may also be implemented according to design and response characteristics of a given application.

In the specific exemplary case where the score is targeted to a specific molecule (such as a biomolecule or macromolecule) or a set of molecules, the energy inputs of the score will generally correspond to enough resonant structures in the target molecule to distinguish it from other molecules in its environment (as discussed above, the energy inputs may, but need not, have the same frequencies as the resonant structures to which they correspond). Since most or all of the energy inputs will resonate the target molecule, while only a subset of the energy inputs will resonate other molecules sharing some but not all of the resonant structures of the target, the target will absorb enough energy from the score to distinguish it. This effect may cause, for example, local heating in the area of the target molecule, breaking one or more bonds in or to the target molecule, or changing a kinetic parameter of a reaction involving the molecule.

In many cases, characteristics of systems including one or more atoms and corresponding bonds may be considered independently. In other applications, it may be appropriate to analyze, compensate for, adjust for, or otherwise consider shifts or changes in characteristics of a first system including one or more atoms responsive to interaction with a second system having one or more atoms or of energy input to the first system of one or more atoms.

For example, one can identify shifts in the resonant longitudinal vibrational frequency of one or more atomic bonds as a result of optical power input, as described in for example, in Andrews and Crisp, "Laser-Induced Vibrational Frequency Shift," bearing a date of 25 Feb. 2005, which is incorporated by reference herein and is appended hereto. This effect may be used to tailor the transfer of energy to a molecule, by adjusting the excitation frequency to match the shift as the vibration increases.

Figure 3:
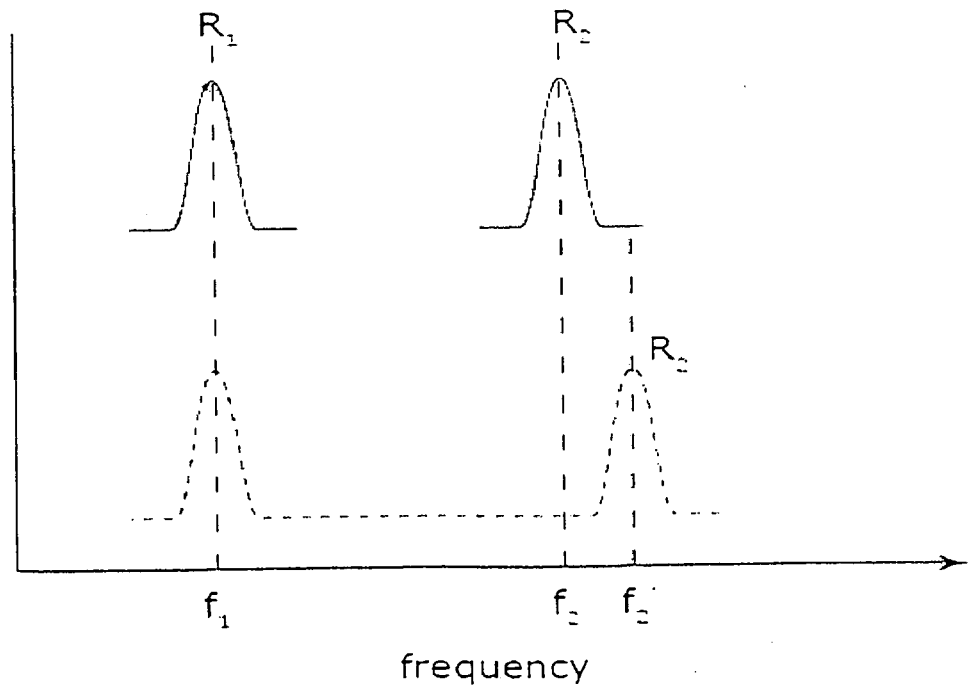
FIG. 3 illustrates how a frequency of one resonant structure may shift as another resonant structure is excited.

FIG. 3 illustrates how the frequency of one resonant structure may shift as a nearby resonant structure is excited. When inputs $R_1$ and $R_2$ are separately applied (solid lines), they resonate structures at frequencies $f_1$ and $f_2$. However, when the structures are coupled in a particular composition, the application of input $R_1$ may shift the resonant frequency $f_2$ to $f_2'$. Thus, that composition may be more efficiently excited by resonating with input $R_1$ and an input $R_2'$ that is frequency shifted relative to input $R_2$. In a similar approach, the frequency of one resonant structure may shift as the resonant structure is subjected to other influences, such as temperature changes. The energy inputs may be varied to accommodate such variations in a similar fashion.

Figure 4:
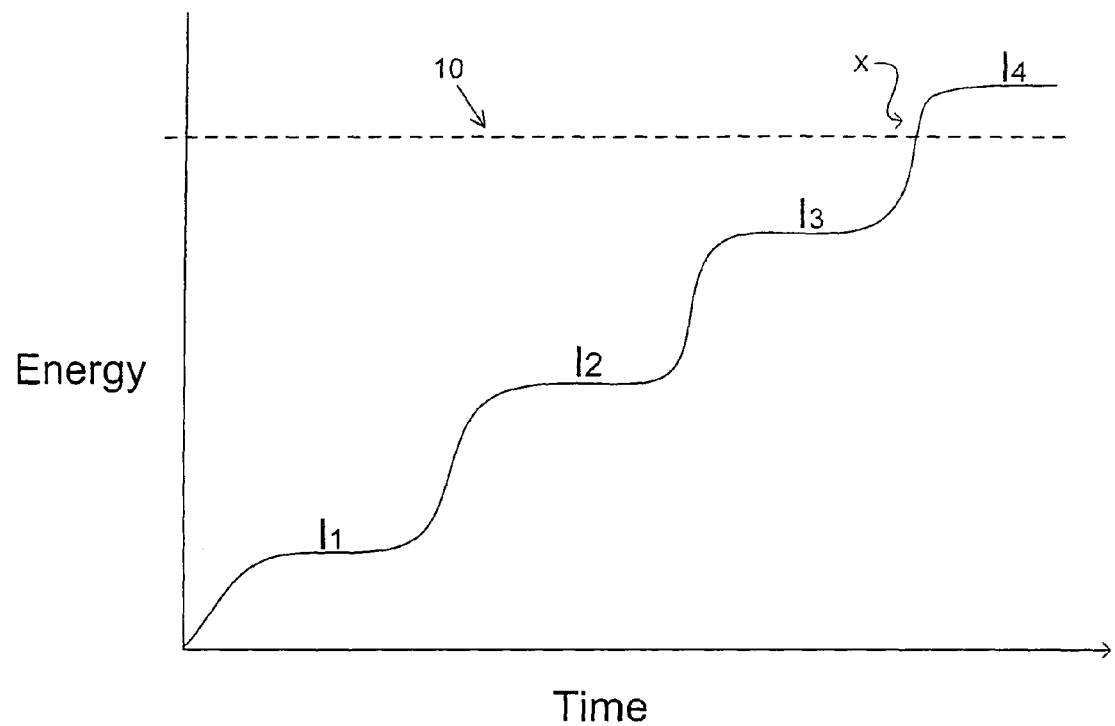
FIG. 4 is a schematic representation of the response of a molecule to a series of energy inputs.

FIG. 4 illustrates schematically how a score may be used to selectively excite a particular molecule sufficiently to break a bond, which can destroy the molecule. As shown, inputs $I_1$, $I_2$, $I_3$, and $I_4$ are applied to the composition in a sequence which may include temporal overlap. Input $I_1$ excites a first resonant structure, adding energy to the molecule. As each additional input excites its own respective resonant structure in the molecule, the energy added increases as shown, until $I_4$ drives the vibration past the breaking strength for a bond (shown schematically as dashed line 10). Each of the individual inputs may be insufficient alone to destroy the molecule, but acting in concert, they do. Where the energy to break the bond is higher than that which would be provided by a combination of less than all four inputs (assuming no increase in the amplitudes of the individual inputs), only molecules having the four resonant structures in sufficient proximity will experience the breaking of the bond (it will of course be understood that this technique is not limited to scores specifying exactly four inputs, but that it may be applied with as few as two inputs or as many as appropriate to achieve the final effect).

This selectivity can be further enhanced by exploiting frequency shifts as discussed above, to more selectively interact with molecules whose resonant structures are responsive to the shifted frequencies. Note that the effect of combining respective inputs to provide cumulative energy input is not limited to breaking bonds as presented in this exemplary embodiment. For example, the approach described herein may also be used to alter kinetic parameters or to achieve any other desired chemical, physical or other effect.

Figure 5:
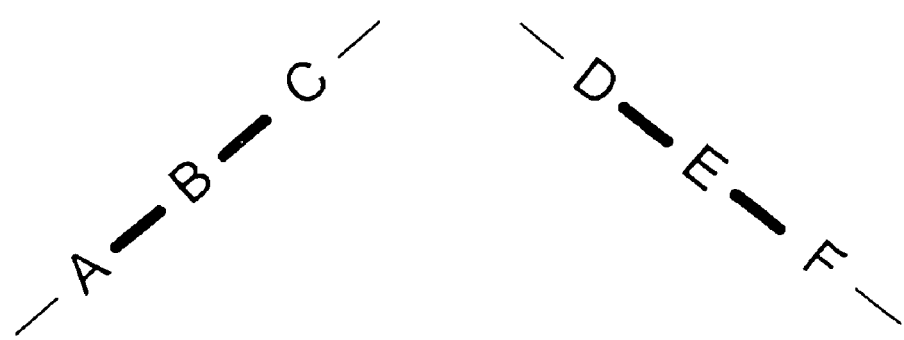
FIG. 5 illustrates diagrammatically excitation to breakage of a bond in a linear molecule.

FIG. 5 illustrates another scenario in which a bond in a molecule having a substantially linear portion can be excited to breakage. As shown, the molecule includes a chain of atoms A, B, C, D, E, and F. Initially, respective inputs excite the A-B and E-F, causing secondary excitation and/or frequency shifting of adjacent bonds B-C and D-E. Subsequent inputs excite the adjacent bonds B-C and D-E. The excitations of the bonds B-C and D-E causes a further excitation and/or frequency shift of center bond C-D. The cumulative effect of the inputs to bonds A-B, B-C, D-E, E-F excites bond C-D. In some applications, the cumulative excitation of bond C-D from the adjacent bonds is sufficient to break bond C-D. In some cases, additional excitation directed at bond C-D is combined with the cumulative excitation of bond C-D from the adjacent bond to produce the intended result, such as severing the C-D bond. Of course, the technique is not limited to molecules having the simple linear structure shown in FIG. 5, but can be applied to any composition in which two sequences of resonant structures can be identified that lead to a common center.

In addition, it may not be necessary to actively excite all of the bonds or other structures along the path to the common center. For example, the excitation of the A-B and E-F bonds shown in FIG. 5 may be sufficient to cause secondary excitation of the B-C and/or D-E bonds without additional energy inputs. In this way, energy inputs targeted to remote structures A-B and E-F may propagate along the molecule, meeting to cause a desired effect at targeted center structure C-D. In such embodiments, the targeted bond need not be exactly at the midpoint between the remote structures as shown in FIG. 5; the timing of the excitation of the remote structures may be adjusted to determine a desired "meeting point" for the propagated excitations.

Moreover, depending upon the amount of energy and the particular characteristics of the bonds and atoms, the inputs to excite the various bonds may be applied substantially simultaneously, may be applied at times that only overlap partially, or that are non-overlapping. Further, certain resonant structures may be "rung up" and "rung down" in a multi-step process by applying excitation and anti-excitation (e.g., damping or canceling) energy inputs as discussed above. Controlling the relative timing, intensities, orientations, or other characteristics of the plurality of energy inputs according to the ring up response, or other transient response characteristics of the resonant structures can increase the selectivity, efficiency, or other parameters of energy transfers to or from the resonant structures. Such techniques may also be useful to create intermediate structures or effects, analogous to the creation of intermediate structures in a multi-step chemical synthesis or reaction.

Figure 6:
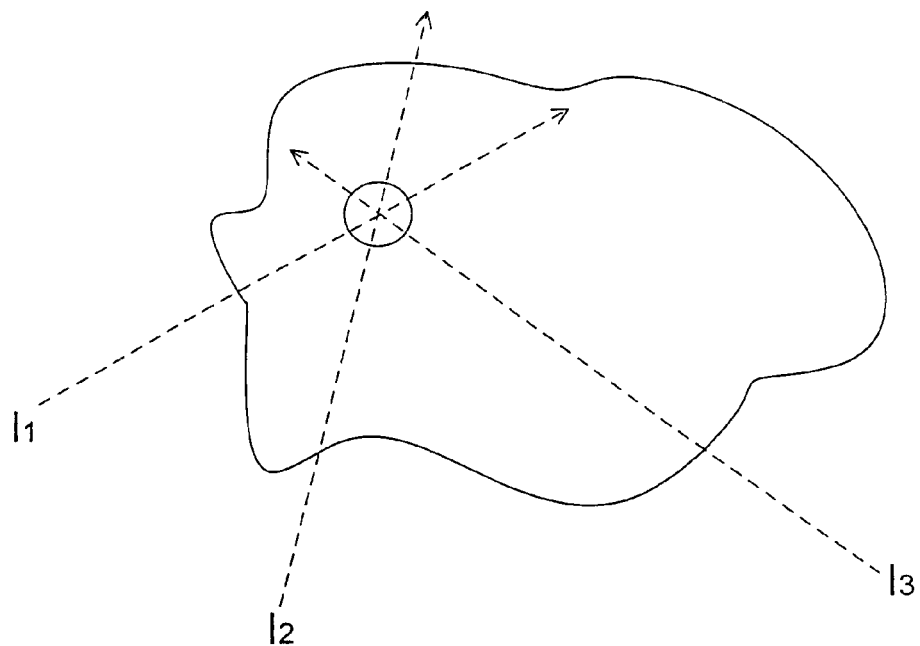
FIG. 6 illustrates diagrammatically the application of multiple intersecting energy inputs to a target voxel.
Figure 7:
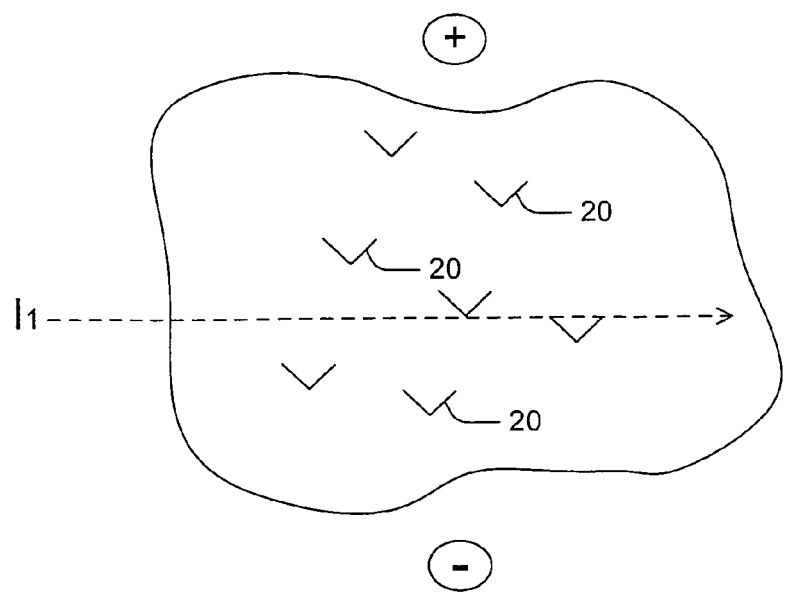
FIG. 7 is a schematic showing the application of an electric field to align resonant structures in a medium.

For certain compositions, transfer of energy to the resonant structures will be a function of the orientation of the resonant structure relative to the direction of the energy input. FIGS. 6 and 7 illustrate two embodiments that allow this relative orientation effect to be exploited.

In FIG. 6, three energy inputs $I_1$, $I_2$, and $I_3$ from different directions converge at a target location (voxel) within a medium containing direction-dependent resonant structures. Since the energy inputs come from different directions, they each affect resonant structures in a different orientation. By selecting an appropriate number of energy inputs in different directions, an arbitrarily high percentage of the target resonant structures can be affected by the beams. These energy inputs need not be simultaneously applied from separate sources, as shown in FIG. 6; they may also be applied by a single source, where either the source or the target material is rotated in order to change the effective direction of the energy input, or where the single source is redirected by means of reflectors, beam splitters, optical fibers, applied fields, or other known energy directing elements. In addition, the energy input(s) may be scanned relative to the material to affect a plurality of voxels within the material. Further, multiple energy inputs need not always intersect as shown in FIG. 6, but may be independently directed according to the needs of a particular application. The plurality of energy inputs shown may have either the same or differing frequency, phase, amplitude, temporal profile, polarization, and/or coherence, depending on the needs of the particular application. Multiple energy inputs may also be used even with non-direction-dependent structures, for example in order to overcome scattering within the medium. Where a plurality of inputs excite a given voxel, from differing locations or orientations, the excitation in the voxel may exceed that of locations outside of the voxel, thereby allowing selective excitation of the voxel at a selected level.

In another aspect, shown in FIG. 7, an additional influence can activate, orient, or otherwise influence resonant structures 20 to interact appropriately with resonant inputs. In the exemplary approach of FIG. 7, an electric field applied to the target material aligns resonant structures 20 prior to application of an energy input. While the exemplary embodiment employs an electric field to influence the resonant structures, any applied field that tends to affect the interaction of the resonant structures with the energy input may be applied, including without limitation a magnetic field, an applied mechanical stress, a lowered or elevated temperature or pressure, a phase change, introduction of an adsorbing surface or catalyst, or the application of another energy input. Rotating a number of resonant structures into a known orientation may allow more efficient excitation, a simpler configuration, or a reduced number of energy inputs (e.g., only $I_1$ as shown in FIG. 7) to resonate the resonant structures appropriately. As previously described in reference to FIG. 6, the applied energy input(s) may be scanned, rotated, or otherwise adjusted relative to the material. In addition, the applied field itself may be scanned, rotated, or otherwise adjusted relative to the target, for example by movement or rotation of the field or by movement or rotation of the target.

Figure 8:
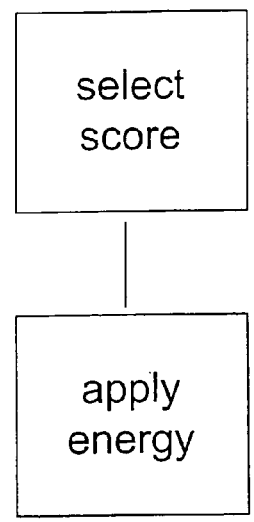
FIG. 8 is a schematic representation of an energy application method.

FIG. 8 shows schematically a method of applying energy. A suitable score is selected by any of a variety of methods, some of which are detailed herein, and then energy is applied to a target in conformance with the score. The score specifies a plurality of energy inputs that apply the energy. The energy may, for example, be applied in the form of one or more electromagnetic beam(s), in which case the score may specify frequency, modulation frequency, phase, amplitude, temporal profile, polarization, and/or coherence for the beam(s).

Figure 9:
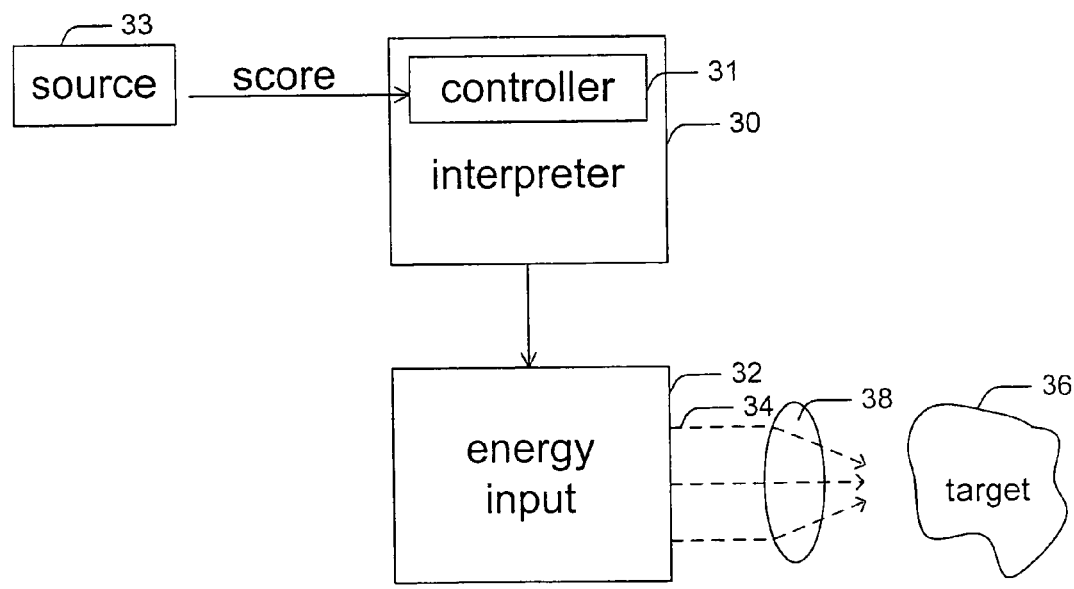
FIG. 9 is a schematic representation of a device for applying energy according to a score.

FIG. 9 shows schematically a device for applying energy in accordance with a score. Interpreter 30 accepts a score which specifies a plurality of energy inputs. The interpreter may include an electronic controller 31 that can receive the score from a source 33, such as a database or library (e.g., the library described below with reference to FIG. 13), a feedback system (e.g., the feedback system described below with reference to FIG. 10), a score generator (e.g., the modeling tool described below with reference to FIG. 11) or other source of a score. The source 33 may be within or integral to the interpreter 30, or external to or remote from the interpreter 30.

Additionally, the source 33 may be located proximate to the interpreter, may be separate from the interpreter, or may be distributed. In one example, the source may be implemented logic or circuitry that also includes logic or circuitry that forms a part of the interpreter. In one example of a distributed source, a remotely located component, such as a central database, provides information relative to the score that is converted by a local component, such as a computer, to data appropriate for use by the interpreter 30. Alternatively, the information relative to the score may be converted by the electronic controller 31 within the interpreter, or may be provided to the interpreter in a format not requiring conversion.

The energy application device may also include a score location component (not shown), which may select a score for conversion by the interpreter, for example from a library of scores, or a score input component (not shown) that accepts a score from a user. In other embodiments, an input component may accept an input composition or structure (e.g., from a user), and return a score that has an effect on the accepted composition or structure or on a portion of the accepted composition or structure, to the interpreter. In some embodiments, the input component may then present the returned score to the user for approval before passing it to the interpreter.

The presented returned score may be represented to the user visually in a variety of manners. For example, the score may be presented graphically as a spectrographic representation, a dynamic model, a spreadsheet, or other user perceivable representation. The representation may also include additional information, such as a visual representation of a different score. Such presentation may provide a visually perceivable contrast to the user, for example by highlighting energy inputs that are added, subtracted, or modified in one score relative to another.

In another approach, the score may be presented audibly to the user. In such a case, each note of the score may be converted to a corresponding audible note that the user can detect. In some cases, it may be appropriate for the correspondence between the notes of the score and the presented audible notes to be established according to a standardized protocol. This can aid a user in detecting patterns and deviations from such patterns by identifying "off-key" audible notes. In one such protocol, a range of frequencies of the input energies can map to a range of audible frequencies, in a linear, logarithmic, or other mapping, such that increases in the input energy frequency can be represented as increases in the audible frequency. Moreover, intensities or amplitudes may also be mapped to provide audible indications of the amplitudes of the notes in the score. One skilled in the art will recognize that other types of mapping or correlations may also be applied. For example, the frequency mapping may be inverted, the various input frequencies may be mapped into subsets of frequencies (e.g., ranges of input frequencies mapped to selected octaves of the audible frequencies), or other types of audible presentations may be developed. Further, in addition to, or in lieu of, a signal audible to a user, the score may be mapped to an acoustic signal detectable by an acoustic receiver that can act as a monitor of the score components.

In another aspect, the information representing the score may be compressed or encrypted according to known techniques. The interpreter may accept an authorization (e.g., a decryption key or authorization code) or may decompress the information to produce a more complete representation of the score before continuing the process, as described below.

The interpreter converts the score into appropriate control instructions for an energy input device 32 (e.g., a laser). The energy input device applies the energy inputs 34 to a target 36. The energy input device may apply energy using either a single or a plurality of beams (e.g., an array of lasers). The energy input device may further comprise optional elements 38 that direct and/or modify the beam (e.g., reflectors, polarizers, optical fibers, lenses, and/or other optical coupling elements).

Figure 10:
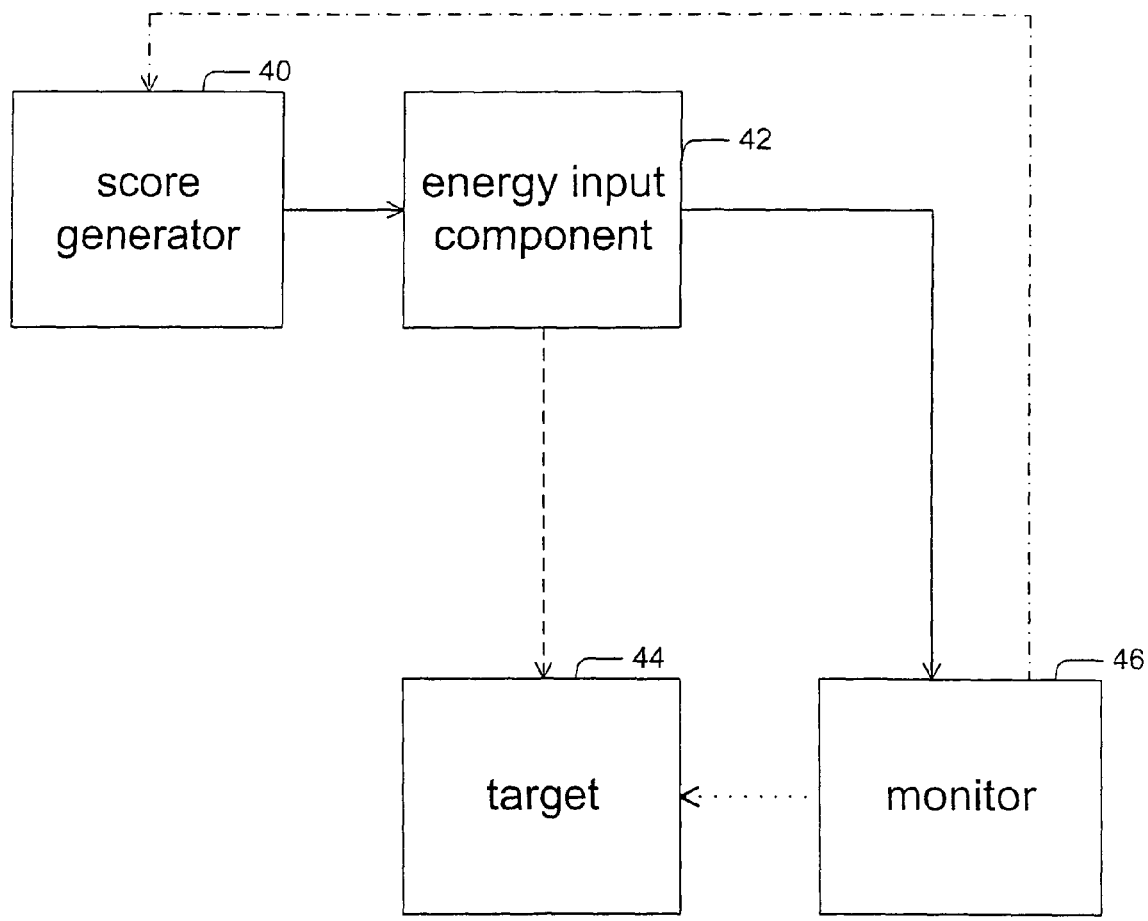
FIG. 10 is a schematic representation of a device with optional monitoring and feedback control for score application.

FIG. 10 shows schematically a device with optional monitoring and feedback control for score application. A score generator 40 (which may include, for example and without limitation, a database of scores, a molecular modeling device that determines resonant frequencies, a database of spectrographs, or another source of scores as described herein) provides a score to an energy input component 42. The energy input component applies energy inputs to a target 44 as specified by the score. In addition, a monitor 46 may observe the effect on the target of the applied energy inputs. In embodiments in which a monitor is present, it may optionally provide feedback to the score generator, which may then provide a new or adjusted score to the energy input component in response to the observations of the monitor. The monitor may be of a type that identifies energy levels, kinetic effects, structural variations, chemical variations or any other appropriate variation in the target 44. For example, thermal imaging can provide an indication of thermal buildup in the target. In another example, an optical beam may pass through or be reflected from the target. As is known, in some materials, the optical transmission or reflection properties (e.g., index or refraction, diffraction phenomena, or absorption) can be a function of stresses, thermal effects, or other effects that may be induced by the input component 42; the monitor uses the optical beam to detect these changed properties, revealing the effects induced by the input component.

In biological applications, scores may be used for diagnostic and/or therapeutic purposes. For example, in embodiments involving the treatment of blood, a monitoring device may be placed over a blood vessel (e.g., in the wrist or on the earlobe), continually monitoring and/or altering blood chemistry as blood flows close to the skin. Alternatively, a fiber optic cable or other physical device for energy transmission may deliver energy impulses deeper into the body. In either case, a substantial portion, or even all, of the entire volume of blood of a patient can be treated in a relatively short amount of time as the blood circulates through a targeted vessel. The monitoring device may, for example, observe and/or chemically modify proteins in the blood. In another embodiment, the monitoring device may continuously monitor blood components such as sugars, triglycerides, or cholesterol, and optionally moderate their levels if they pass a threshold.

Figure 11:
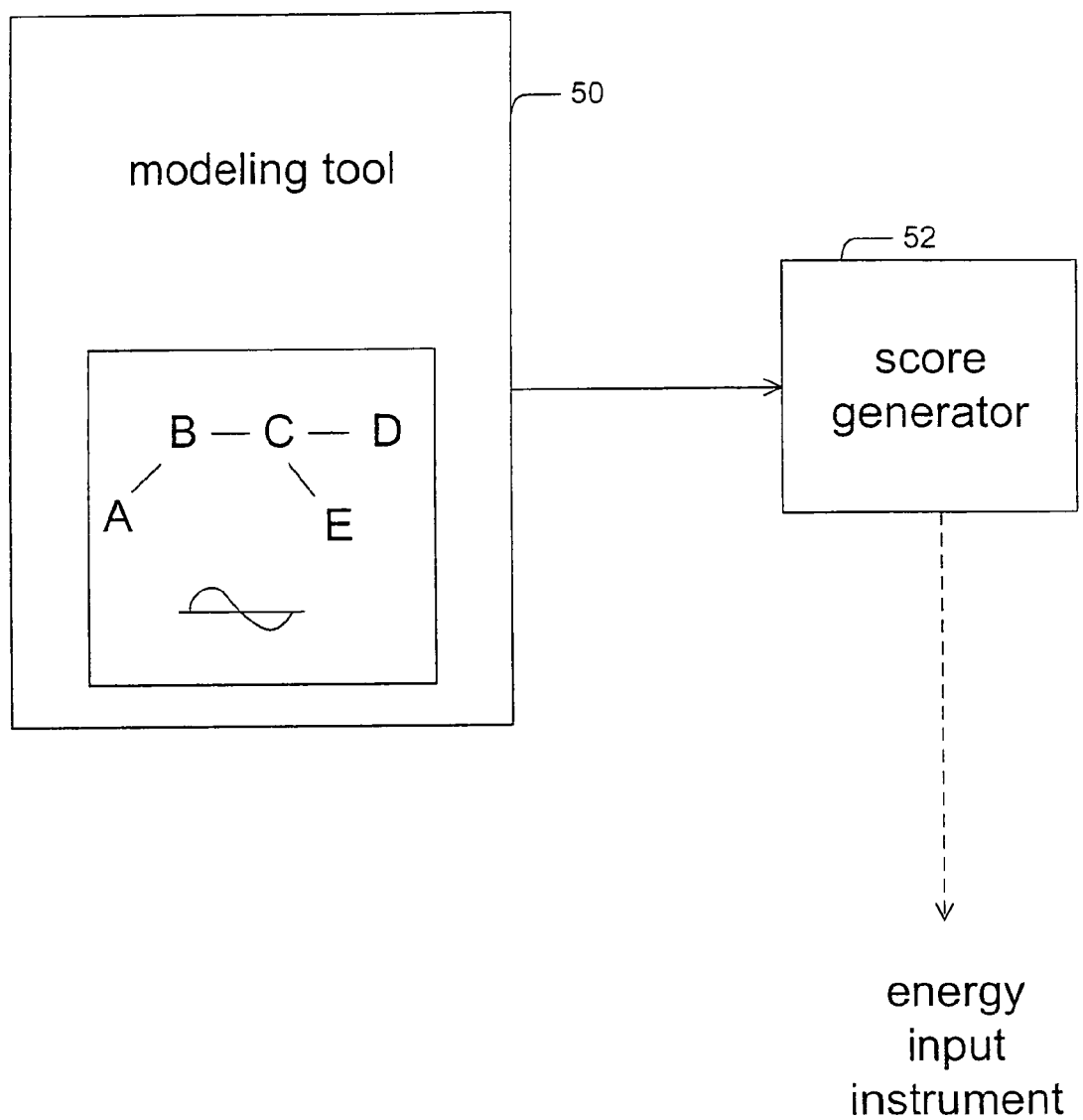
FIG. 11 is a schematic representation of an apparatus for generating score.

FIG. 11 shows schematically an apparatus for generating scores based on computational modeling of resonant structures. A modeling tool 50 generates a model of a structure (e.g., a molecular model of a chemical composition, or a quantum mechanical model of the energy levels of a quantum dot) in order to determine its predicted resonances. A score generator 52 then incorporates the predicted resonances into a score. The generated score may be passed to an energy input instrument.

Figure 12:
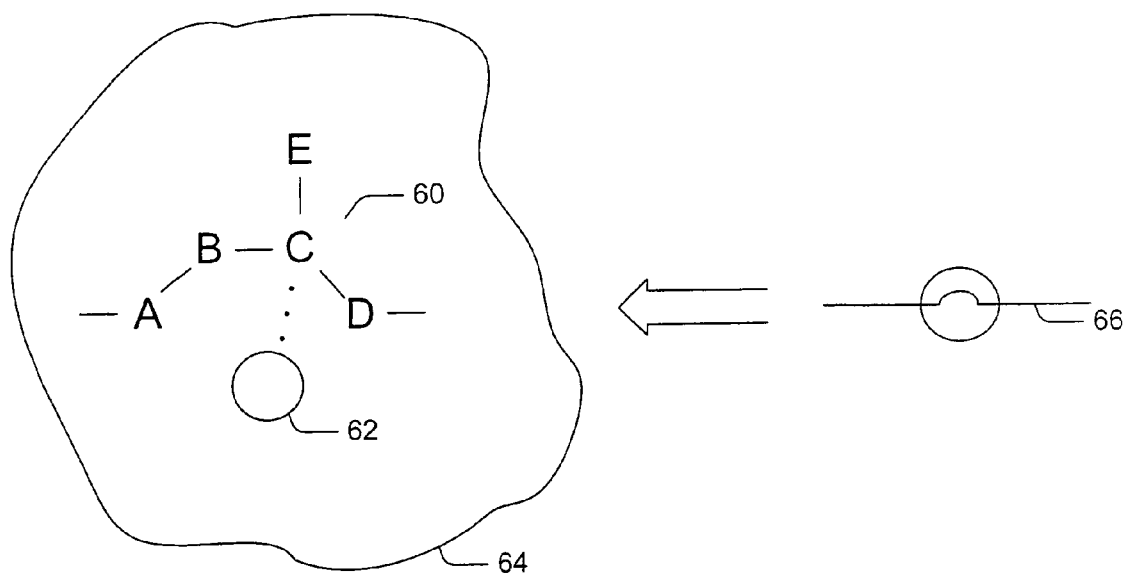
FIG. 12 illustrates a system for introducing a chemical agent into a medium.

FIG. 12 shows schematically a system for introducing a chemical agent into a medium, which may in some embodiments be used for therapeutic purposes. As shown, the chemical agent comprises a composition 60 bound to an optional carrier 62, which is located within a medium 64. Energy input device 66 applies a score to the medium. In some embodiments, this score is selected to sever the bond between the composition and the carrier, thereby releasing the composition into the medium. In other embodiments, the applied score activates the composition directly, for example by breaking one or more bonds of the composition, ablating material surrounding the composition, heating material surrounding the composition, or reacting with material surrounding the composition. In some embodiments, these techniques may be used to deliver a catalyst or other chemical agent to difficult-to-reach areas. For example, a cleaning or recharging agent could be dispersed throughout a water treatment system in an inert form, and then rendered active by application of a score to the whole system. Such an embodiment may in some cases allow more uniform application of the cleaning or recharging agent, particularly in high-surface-area systems where a reactive agent may be difficult to disperse throughout the system.

For use in vivo, the optional carrier or the composition may have an affinity to a selected substance or tissue, which forms the medium of FIG. 12. The optional carrier or the composition may be placed directly in a particular tissue (e.g., by injection into the tissue), or may be introduced into the body and allowed to accumulate at the selected tissue. For example, an iodine-containing composition may be introduced into the body orally or by injection into the bloodstream, and allowed to accumulate in the thyroid gland. A score comprising infrared energy inputs (to which the body is substantially transparent) may then be used to heat the iodine-containing composition, thereby ablating a tumor and/or a portion of the thyroid gland itself. Other compositions or carriers may similarly be chosen to accumulate in other tissues (e.g., calcium in the bones or teeth or organic compounds in the liver), and then activated by application of a score (e.g., to release a stimulant to cell division and/or growth). Inhaled compositions, optionally bound to fine carriers, may be distributed to the alveoli for treatment of the lungs.

Figure 13:
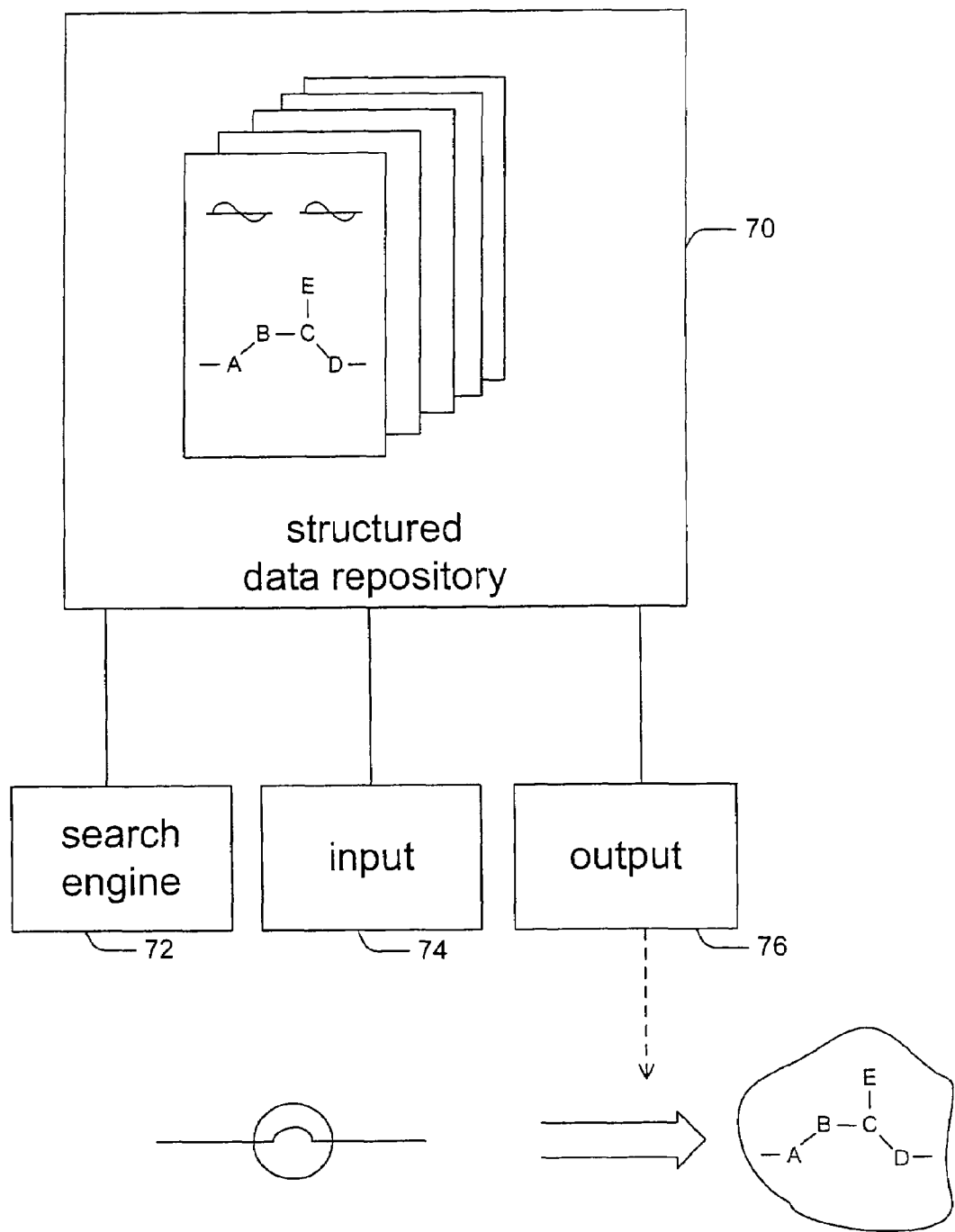
FIG. 13 is a schematic representation of a library of excitation energy specifications.

FIG. 13 shows schematically a library of excitation energy specifications, comprising a structured data repository 70 comprising a plurality of score records. Each score record includes descriptors for a plurality of energy inputs, a descriptor for associated composition(s) affected by the plurality of energy inputs, and optionally a descriptor describing the effect of the plurality of energy inputs on the composition. The energy input descriptors describe at least one of frequency, modulation frequency, phase, amplitude, temporal profile, polarization and direction for each energy input. The library may also include additional features such as a search engine 72, an input component 74, and/or an output component 76. If provided, the output component may provide a user with a score record for download, for example so that it may be used to direct an energy input device to play the score in order to affect the associated composition. The library may be used to screen for a composition, by accessing the library to locate a score record for the composition, applying the energy inputs described by the energy input descriptors of the score record to a medium, and observing the medium for reaction of the composition to the applied inputs. The library may also be used to excite the composition, by accessing the library to locate a score record for the composition and applying the energy inputs described by the score record to the composition (e.g., to destroy the composition). Alternatively, the selected score record may comprise a descriptor of a composition sharing a functional group with the composition to be excited.

Those having skill in the art will recognize that the state of the art of circuit design has progressed to the point where there is typically little distinction left between hardware and software implementations of aspects of systems. The use of hardware or software is generally a design choice representing tradeoffs between cost, efficiency, flexibility, and other implementation considerations. Those having skill in the art will appreciate that there are various vehicles by which processes, systems and/or other technologies involving the use of logic and/or circuits can be effected (e.g., hardware, software, and/or firmware), and that the preferred vehicle will vary with the context in which the processes, systems and/or other technologies are deployed. For example, if an implementer determines that speed is paramount, the implementer may opt for a mainly hardware and/or firmware vehicle. Alternatively, if flexibility is paramount, the implementer may opt for a mainly software implementation. In these or other situations, the implementer may also opt for some combination of hardware, software, and/or firmware. Hence, there are several possible vehicles by which the processes, devices and/or other technologies involving logic and/or circuits described herein may be effected, none of which is inherently superior to the other. Those skilled in the art will recognize that optical aspects of implementations may require optically-oriented hardware, software, and or firmware.

The foregoing detailed description has set forth various embodiments, some of which incorporate logic and/or circuits, via the use of block diagrams, flow diagrams, operation diagrams, flowcharts, illustrations, and/or examples. Insofar as such block diagrams, operation diagrams, flowcharts, illustrations, and/or examples contain one or more functions, operations, or data structures to be performed, manipulated, or stored by logic and/or circuits, it will be understood by those within the art that each such logic and/or circuit can be embodied, individually and/or collectively, by a wide range of hardware, software, firmware, or virtually any combination thereof. For example, some embodiments of the subject matter described herein may be implemented via Application Specific Integrated Circuits (ASICs), Field Programmable Gate Arrays (FPGAs), digital signal processors (DSPs), or other integrated formats. However, those skilled in the art will recognize that other embodiments disclosed herein can be equivalently implemented in whole or in part in standard integrated circuits, as one or more computer programs running on one or more computers (e.g., as one or more programs running on one or more computer systems), as one or more programs running on one or more processors (e.g., as one or more programs running on one or more microprocessors), as firmware, as analog circuitry, or as virtually any combination thereof, and that designing the circuitry and/or writing the code for the software and or firmware would be well within the skill of one of skill in the art in light of this disclosure. In addition, those skilled in the art will appreciate that the operations, functions, and data (e.g., scores) described herein are capable of being distributed or stored in a variety of signal bearing media. Examples of a signal bearing media include, but are not limited to, recordable type media such as floppy disks, hard disk drives, CD ROMs, digital tape, and computer memory, and transmission type media such as digital and analog communication links using TDM or IP based communication links (e.g., packet links). The choice of signal bearing media will generally be a design choice representing tradeoffs between cost, efficiency, flexibility, and other implementation considerations in a particular context, and none of these signal bearing media is inherently superior to the other.

The invention claimed is:

1. A method of characterizing a target molecule or group of molecules in an environment, comprising:
   identifying a group of resonant structures within the target, wherein:
      each resonant structure in the group possesses at least one characteristic resonant frequency;
      the characteristic resonant frequency of a shiftable resonant structure in the group can be shifted by exciting a shifting resonant structure in the group; and
      the group of resonant structures is substantially absent from nontarget molecules in the environment;
   determining a score specifying a set of applied frequencies that, when applied in sequence to the target,
      shift the characteristic resonant frequency of the shiftable resonant structure in the group through excitation of the shifting resonant structure in the group;
      excite the shiftable resonant structure at its shifted resonant frequency; and
      selectively change the energy or state of at least a portion of the target relative to its environment; and
   applying the set of applied frequencies to the environment of the target molecule.

2. The method of claim 1, wherein the set of applied frequencies, when applied in sequence to the target, shifts the resonance of and excites a plurality of the resonant structures at their respective shifted resonances.

3. The method of claim 1, wherein determining a set of applied frequencies comprises computational modeling of the target.

4. The method of claim 1, wherein determining a set of applied frequencies comprises applying a plurality of sets of applied frequencies to the environment and observing effects of each of the plurality of sets on the target.

5. The method of claim 1, wherein determining a set of applied frequencies comprises spectroscopically observing the target.

6. The method of claim 1, wherein the target comprises a biomolecule.

7. The method of claim 1, wherein the target comprises a nucleotide or a protein.

8. The method of claim 1, wherein the target comprises a crystal.

9. The method of claim 1, wherein the target comprises a complex of molecules.

10. The method of claim 1, wherein the identified group of resonant structures comprises at least 4 resonant structures.

11. The method of claim 1, wherein the identified group of resonant structures comprises at least 10 resonant structures.

12. The method of claim 1, wherein the identified group of resonant structures comprises at least 36 resonant structures.

13. The method of claim 1, wherein the resonant structures of the identified group are contiguous within a molecule.

14. The method of claim 1, wherein the shiftable resonant structure and the shifting resonant structure share an atom.

15. The method of claim 1, wherein the shiftable resonant structure and the shifting resonant structure do not share any atoms.

16. The method of claim 1, wherein the score specifies application of an electromagnetic beam as an energy input.

17. The method of claim 16, wherein the electromagnetic beam has at least one characteristic selected from the group consisting of:
   a selected set of frequencies;
   a selected set of modulation frequencies;
   a selected set of phases;
   a selected set of amplitudes;
   a selected temporal profile;
   a selected set of polarizations; and
   a selected direction.

18. The method of claim 17, wherein the selected set of frequencies is approximately monochromatic.

19. The method of claim 18, wherein the electromagnetic beam is coherent.

20. The method of claim 18, wherein the electromagnetic beam is incoherent.

21. The method of claim 17, wherein the selected set of frequencies comprises a plurality of local maxima.

22. The method of claim 17, wherein the selected set of modulation frequencies comprises a plurality of local maxima.

23. The method of claim 17, wherein the electromagnetic beam is coherent.

24. The method of claim 17, wherein the electromagnetic beam is incoherent.

25. The method of claim 17, wherein the selected set of frequencies comprises at least two frequencies, and wherein the at least two frequencies have differing amplitudes.

26. The method of claim 17, wherein the selected set of modulation frequencies comprises at least two frequencies, and wherein the at least two frequencies have differing amplitudes.

27. The method of claim 17, wherein the temporal profile is characterized by a selected beam duration.

28. The method of claim 17, wherein the temporal profile is characterized by a selected change in frequency, modulation frequency, phase, amplitude, polarization, or direction during a selected time interval.

29. The method of claim 17, wherein the electromagnetic beam is polarized.

30. The method of claim 16, wherein the electromagnetic beam is an infrared beam.

31. The method of claim 16, wherein the electromagnetic beam is amplitude modulated.

32. The method of claim 16, wherein the electromagnetic beam is frequency modulated.

33. The method of claim 1, wherein the score specifies application of a plurality of electromagnetic beams.

34. The method of claim 33, wherein the plurality of electromagnetic beams differ in frequency, modulation frequency, phase, amplitude, temporal profile, polarization or orientation.

35. The method of claim 33, wherein the plurality of electromagnetic beams intersect at a target location.

36. The method of claim 1, wherein the score specifies applying a field to the environment, wherein the field acts to preferentially orient at least a portion of the target.

37. The method of claim 36, wherein the field is selected from the group consisting of an electric field, a magnetic field, an electromagnetic field, a mechanical stress, a mechanical strain, a lowered or elevated temperature, a lowered or elevated pressure, a phase change, an adsorbing surface, a catalyst, an energy input, and combinations thereof.

* * * * *